United States Patent [19]
Kaldany

[11] Patent Number: 5,695,482
[45] Date of Patent: Dec. 9, 1997

[54] UV TREATED CATHETER

[75] Inventor: Antoine Kaldany, Chestnut Hill, Mass.

[73] Assignee: InterMED, Inc., Chestnut Hill, Mass.

[21] Appl. No.: 259,796

[22] Filed: Jun. 15, 1994

Related U.S. Application Data

[62] Division of Ser. No. 984,393, Dec. 2, 1992, Pat. No. 5,334,171, which is a division of Ser. No. 734,478, Jul. 23, 1991, Pat. No. 5,222,949.

[51] Int. Cl.⁶ .................................. A61M 25/00
[52] U.S. Cl. .................. 604/280; 604/20; 606/15; 606/16
[58] Field of Search ................ 604/280, 282, 604/21, 264.2; 128/656, 658, 659, 662.06; 606/2, 3, 7, 8, 11, 15, 16

[56] References Cited

U.S. PATENT DOCUMENTS

| | | |
|---|---|---|
| 1,596,754 | 8/1926 | Moschelle . |
| 2,268,321 | 12/1941 | Flynn . |
| 2,458,305 | 1/1949 | Sanders . |
| 3,014,501 | 12/1961 | Jacobi . |
| 3,122,171 | 2/1964 | Britton et al. . |
| 3,297,055 | 1/1967 | Beck . |
| 3,479,670 | 11/1969 | Medell . |
| 3,498,286 | 3/1970 | Polanyi et al. ............... 128/2 |
| 3,548,882 | 12/1970 | Rinker . |
| 3,598,126 | 8/1971 | Hoeltzenbeim . |
| 3,670,733 | 6/1972 | Guerster . |
| 3,861,972 | 1/1975 | Glover et al. . |
| 3,957,054 | 5/1976 | McFarlane . |
| 4,445,892 | 5/1984 | Hussein et al. ............... 604/101 |
| 4,511,209 | 4/1985 | Skutnik ..................... 350/96.34 |
| 4,516,972 | 5/1985 | Samson . |
| 4,519,390 | 5/1985 | Horne ..................... 606/15 |
| 4,639,252 | 1/1987 | Kelley et al. . |
| 4,660,925 | 4/1987 | McCaughan, Jr. . |
| 4,661,396 | 4/1987 | Andorf et al. . |
| 4,662,368 | 5/1987 | Hussein et al. . |
| 4,662,404 | 5/1987 | LeVeen et al. . |
| 4,690,175 | 9/1987 | Ouchi et al. . |
| 4,691,709 | 9/1987 | Cohen ........................ 128/667 |
| 4,732,448 | 3/1988 | Goldenberg . |
| 4,737,153 | 4/1988 | Shimamura et al. . |
| 4,782,818 | 11/1988 | Mori . |
| 4,832,681 | 5/1989 | Lenck . |
| 4,842,590 | 6/1989 | Tanabe et al. . |
| 4,854,315 | 8/1989 | Stack et al. . |
| 4,860,743 | 8/1989 | Abela . |
| 4,862,886 | 9/1989 | Clarke et al. . |
| 4,898,591 | 2/1990 | Jang et al. . |
| 4,899,787 | 2/1990 | Ouchi et al. . |

(List continued on next page.)

FOREIGN PATENT DOCUMENTS

| | | |
|---|---|---|
| 0 362 497 | 4/1990 | European Pat. Off. . |
| 2843061 | 4/1980 | Germany . |
| 1 567 122 | 5/1980 | United Kingdom . |

OTHER PUBLICATIONS

Bergman et al., "Minimum Performance Standards for Double–Lumen Subclavian Cannulas for Hemodialysis," *Asaio Transactions*, vol. 32, No. 1, Jul./Sep. 1986, pp. 500–502.

Maki et al., "Risk Factors for Infusion–Related Phlebitis with Small Peripheral Venous Catheters," *Annals of Internal Medicine*, vol. 114, No. 10, May 15, 1991, pp. 845–854.

*Primary Examiner*—Michael Powell Buiz
*Assistant Examiner*—Ronald K. Stright, Jr.
*Attorney, Agent, or Firm*—Hamilton, Brook, Smith & Reynolds, P.C.

[57] ABSTRACT

A unitary, flexible, substantially noncollapsible catheter tube of biocompatible material is comprised of hard and soft regions. The hard regions can be ring shaped or helical. The hard regions provide sufficient rigidity to the tube to prevent collapse under normal usage as the interior and exterior pressures vary. The soft regions provide sufficient flexibility to allow contoured placement of the tube. The hard regions can be created by exposing a polymer in the tube to radiation. The hard regions can also be created by periodically adding a harder material to the tube.

17 Claims, 4 Drawing Sheets

U.S. PATENT DOCUMENTS

| | | | |
|---|---|---|---|
| 4,900,314 | 2/1990 | Quackenbush . | |
| 4,945,894 | 8/1990 | Kawashima | 128/6 |
| 4,950,258 | 8/1990 | Kawai et al. . | |
| 4,955,862 | 9/1990 | Sepetka . | |
| 4,963,556 | 10/1990 | McCaughan . | |
| 4,985,022 | 1/1991 | Fearnot et al. . | |
| 5,005,180 | 4/1991 | Edelman et al. | 372/57 |
| 5,019,040 | 5/1991 | Itaoka et al. | 604/95 |
| 5,053,033 | 10/1991 | Clarke | 606/3 |
| 5,092,841 | 3/1992 | Spears | 604/96 |
| 5,147,353 | 9/1992 | Everett . | |
| 5,150,096 | 9/1992 | Khoury | 606/15 |
| 5,151,096 | 9/1992 | Khoury | 606/15 |
| 5,176,674 | 1/1993 | Hofmann | 606/7 |
| 5,188,632 | 2/1993 | Goldenberg | 606/7 |
| 5,193,526 | 3/1993 | Daikuzono . | |
| 5,199,951 | 4/1993 | Spears | 604/96 |
| 5,207,669 | 5/1993 | Baker et al. . | |

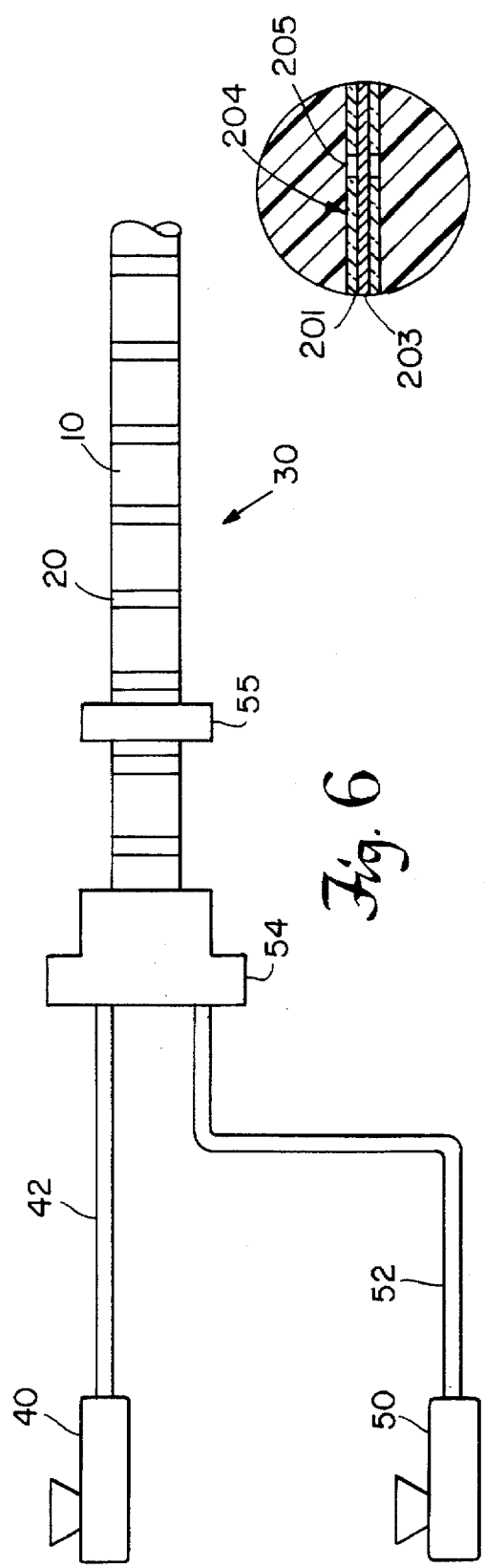
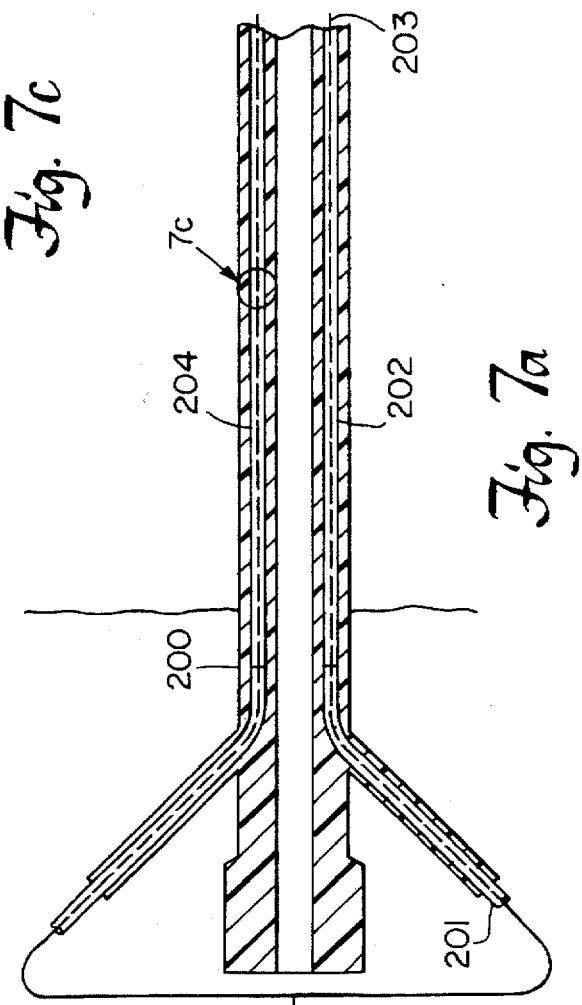
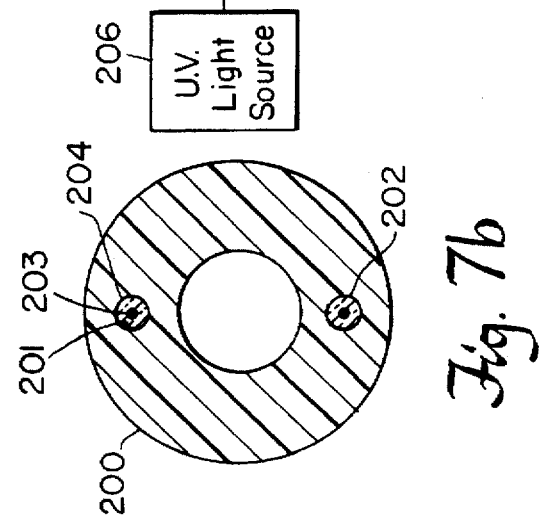

UV TREATED CATHETER

This application is a division of application Ser. No 07/984.393 filed Dec. 2, 1992 now U.S. Pat. No. 5,334,171 issued Aug. 2, 1994, which is a divisional of Ser. No. 07/734,478 filed Jul. 23, 1991 (now U.S. Pat. No. 5,222,949 issued Jun. 29, 1993).

BACKGROUND OF THE INVENTION

Flexible tubing is used in many medical applications. The flexing of the tube permits contoured placement. In a medical context, flexible tubing is required for use in catheter devices to prevent damage when inserted into a body lumen. However, flexible tubing has a continuing problem with collapse. To prevent collapse, catheters require adequate stiffness to effect insertion into the body lumen and to resist collapse as the respective interior and exterior pressures of the tube vary.

Catheter tubes are typically used for nasogastric suction, for the administration of intravenous fluids and blood, for hemodialysis and other blood handling techniques, for gastro-duodenal feeding tubes, suction tubing, and tracheostomy tubing. Kinking of such tubing can cause blocking of the catheter. When kinking or suction induced collapse of the tube walls occur, flow ceases in the tubing and the consequences can be serious—even fatal.

Knotting can also occur in tubing induced into a body cavity. Such knots make it impossible to withdraw the tubing without resorting to surgery.

Catheters can be a source of infection. This problem is exacerbated the longer the catheter remains in the body. Organisms can enter the body at the skin surrounding the catheter or through the interior of the catheter.

SUMMARY OF THE INVENTION

Accordingly, a need exists in the medical field for tubing which is flexible yet includes adequate stiffness to prevent collapse during normal use. The invention is directed to a flexible, non-collapsible tube comprising a flexible region including a first composition and a hardened region of said first composition. The flexible region permits contoured placement of the tube in a medical context. The hardened region of the tube provides sufficient rigidity to prevent collapse of the tube during long term use. In the preferred embodiment, the tube is comprised of a polymer such as polyurethane with polybutadiene. The hardened region can further comprise a plurality of ring shaped volumes. Also, the hardened region can comprise a helically shaped volume. The hardened regions can be formed by exposing the tube to radiation. This radiation can be ultra-violet energy or thermal energy. The tube can further comprise additional radio-opaque material whenever necessary to permit positioning and placement under fluoroscopy and easier verification of position by a simple x-ray. Also, the hardened regions can be hardened in vivo. A means can be provided to sterilize the catheter in vivo. A second embodiment of the flexible, non-collapsible catheter for insertion in a body lumen can comprise a flexible region including a first composition and a hardened region including a second composition hardened by exposure to radiation.

The flexible tube of the invention can be manufactured by (a) extruding a biocompatible plastic material having a substantially continuous composition to form a tubular plastic member and (b) exposing portions of a plastic member to radiation to expose the hardened portions. As noted previously, the radiation can be ultraviolet energy or thermal energy, but is not limited thereto. For example, ring shaped regions of the tube can be hardened to create a plurality of interspaced hardened and flexible regions. Also, a helically shaped area of the tube can be exposed to produce a hardened portion in that shape.

Thus, a flexible, contourable tube is created with sufficient stiffness and rigidity to resist collapse of the tube. The flexibility permits accommodation with the variation and the anatomic difference between patients and prevents tissue damage by conforming to the vascular architecture of the individual. Moreover, the stiffness is sufficient to permit easy insertion and to prevent collapse of the tube. Thus, adequate blood flows are assured and adequate predictable fluid infusion rates over a broad range of clinical applications are permitted. A specific patient's requirements can be tailored at the bedside. For example, unlike conventional catheters which use a metallic coil to provide tube hardening, a physician could insert a specific length of the catheter of the invention into a patient without exposing body lumens to a sharp metal edge. The hardened areas assure obstruction prevention despite shifts in the patient's position and/or application of negative suction forces for sustaining high blood flow during procedures such as hemodialysis, hemofiltration, hemoprofusion, and plasmapheresis. The device is easy to manipulate and simple and inexpensive to manufacture. The device can also be used as a radio-opaque, low cost surgical drain.

The integral construction of the tube creates both a smooth interior, as well as exterior, diameter. Thus, the tube is very compact. The simple construction permits the use of inexpensive manufacturing techniques.

The above and other features of the invention including various novel details of the construction and combinations of parts will now be more particularly described with reference to the accompanying drawings as pointed out in the claims. It will be understood that the particular device embodying the invention is shown byway of illustration only and not as a limitation of the invention. The principles and features of this invention will be employed in varied and numerous embodiments without departing from the scope of the invention.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1b illustrates a longitudinal cross-sectional view of FIG. 1a.

FIG. 2b illustrates a longitudinal, cross-sectional view of the invention of FIG. 2a.

FIG. 3 illustrates a horizontal, cross-sectional view of FIG. 2a.

FIG. 6 illustrates an extrusion device for manufacturing a second embodiment of the flexible, non-collapsible tube of the invention including a flexible area comprised of a first material and a hardened area comprised of a second material.

FIG. 7(a) illustrates a longitudinal cross-sectional view of an in vivo sterilization catheter.

FIG. 7(b) illustrates a horizontal cross-sectional view of the invention of FIG. 7(a).

FIG. 7(c) is an enlarged view of the cross-section of FIG. 7(a).

DETAILED DESCRIPTION OF THE INVENTION

Figure 1A:
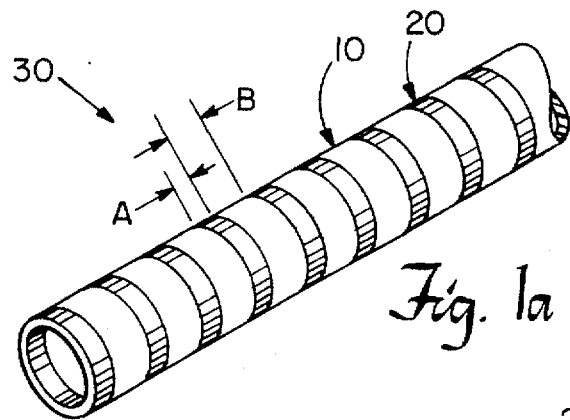
FIG. 1a illustrates the flexible, non-collapsible tube of the invention with ring shaped hardened areas.
Figure 1B:
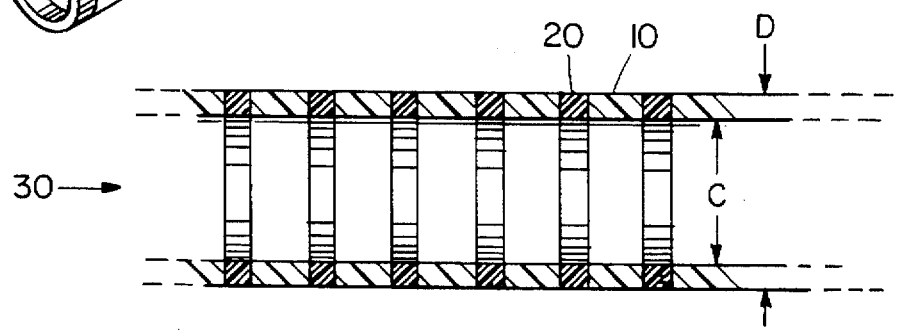

FIGS. 1a and 1b illustrate a first embodiment of the invention. FIG. 1a shows a schematic view of the flexible, noncollapsible biocompatible tube 30. Tube 30 is comprised of a hardenable polymer, such as polyurethane with polybutadiene, which stiffens when exposed to ultraviolet energy or thermal energy. As can be seen in FIG. 1a, flexible section 10, having a length B, provides adequate surface area to permit flexing of the tube around small radii curves. This allows insertion and placement without vascular wall injury or discomfort to the patient. Moreover, the flexible volumes 10 are interspersed with the hardened volumes 20. These hardened regions provide sufficient stiffness to prevent collapse which would result in the obstruction of the tube opening or lumen. Thus, a tube constructed as shown in FIG. 1a can be used to infuse or suck fluids and blood products from veins, arteries, respiratory and congestive conduits for long periods of time.

Polyurethane, which is radioopaque, is useful in determining the placement of the catheter. Other radioopaque materials could also be added to the catheter to assist in locating the catheter position.

FIG. 1b shows the longitudinal cross-section of the schematic illustration of tube 30. As noted in the discussion of FIG. 1a, B represents the length of flexible section 10 and A represents the length of hardened section 20. The integral unitary composition of tube 30 creates a compact, smooth walled coupling device.

Prior catheters used a soft polymeric tube structure with internally reinforced stainless steel or polymeric springs. These springs increased the cost of the tubes substantially and reduced the efficiency of the tube by reducing the inner diameter and increasing the catheter wall thickness. By comparison, the interior and exterior diameters C and D, respectively, of the invention are constant along the length of the tube 30. The length and caliber (or gauge) of the tube will depend on the intended application. Given its simplicity, flexibility and relative low cost, construction can fit a gamut of applications for various lengths and diameters.

The ratio of lengths A and B, will vary in accordance with the specific application. For instance, hemodialysis catheters would have a regular sequential structure whereby portions A would be discrete bands about 1.5 mm wide alternating with portions B which would be discrete bands about 3 mm wide. The ratio of A/B would therefore be about ½ for hemodialysis applications.

In some instances, i.e. central lines for intravenous feeding and/or drug infusion, the hardened portions need not be present along the whole length of the catheter. Ideally, the hardened portions would be restricted to the indwelling (or inserted/intravascular) portion of the catheter, hence allowing a highly flexible portion to extrude, which would be easy to fix or position, providing the patient with minimal discomfort.

Figure 2A:
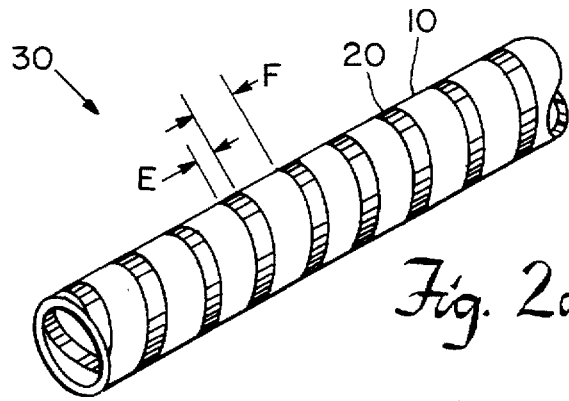
FIG. 2a illustrates the flexible, non-collapsible tube of the invention including a helically shaped hardened area.
Figure 2B:
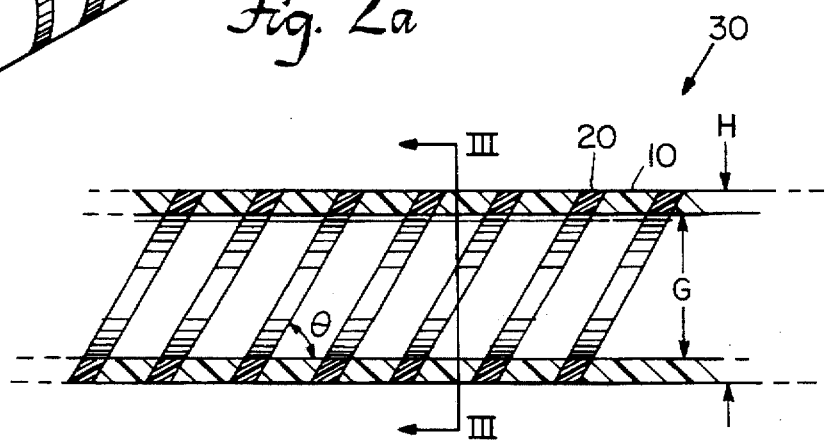

FIGS. 2a and 2b illustrate a second embodiment of the flexible, noncollapsible tube 30. Both the flexible area 10 and the hardened area 20 are in the shape of a helix. E and F represent the length of sections 20 and 10 respectively along the longitudinal axis. The respective areas form an angle θ with the longitudinal axis of the tube 30. FIG. 2b illustrates a longitudinal cross-sectional view of the embodiment of FIG. 2a. As with the ring-shaped embodiment of FIGS 1a and 1b, the helical embodiment of FIGS. 2a and 2b create inner and outer diameters which are smooth along their longitudinal lengths. G represents the inner diameter of the tube whereas H represents the outer diameter of the tube.

Figure 3:
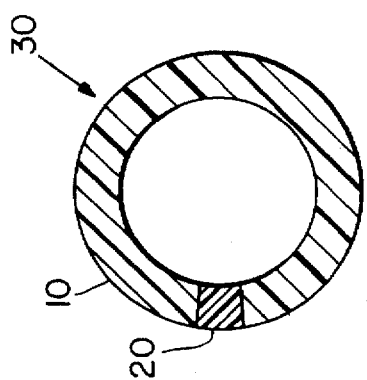

FIG. 3 illustrates a horizontal cross-section of the tube of FIG. 2b with a helical hardened section. As can be seen from FIG. 3, the horizontal cross section reveals that hardened section 20 comprises a small section of tube 30 with respect to the flexible section 10.

Medical tubes and catheters, surrounded as they are by live organs and tissues, are usually not subjected to a great deal of direct stress and strain. The most "pressure" one can expect would be a patient's weight.

When a hollow tube of homogenous material is subjected to bending, material outside the bend radius of the neutral axis is subjected to tensile stress proportional to its distance from the neutral axis. Conversely, material inside the neutral axis is subjected to compressive stress. These stresses cause the material to stretch and compress in accordance with Hooke's law allowing bending to take place.

These stresses also impart a collapsing force on the tube proportional to the ratio $R_t/R_b$, where $R_t$ is the radius of the tube and $R_b$ is the radius of the bend. The ability of the tube to resist this collapsing force is proportional to the ratio $R_t/W$, where W is the wall thickness of the tube.

Therefore, in general terms, the non-collapsing force on the tube of homogeneous material is limited by the wall thickness of the tube; the smaller the bend radius the thicker the wall that must be used.

In the case of a tube selectively reinforced by a spiral or a series of rings of harder material, the collapse strength of the tube is increased. This permits the use of a smaller bend radius and/or a thinner walled tube than a tube of homogeneous material.

Some of the advantages of this type of tubing over homogeneous tubing as related to catheter usage are tighter bend radii for anatomical placement, larger inside diameter for a given outside diameter permitting greater fluid flow, and increased collapse resistance from body weight and vacuum aspiration.

Figure 4A:
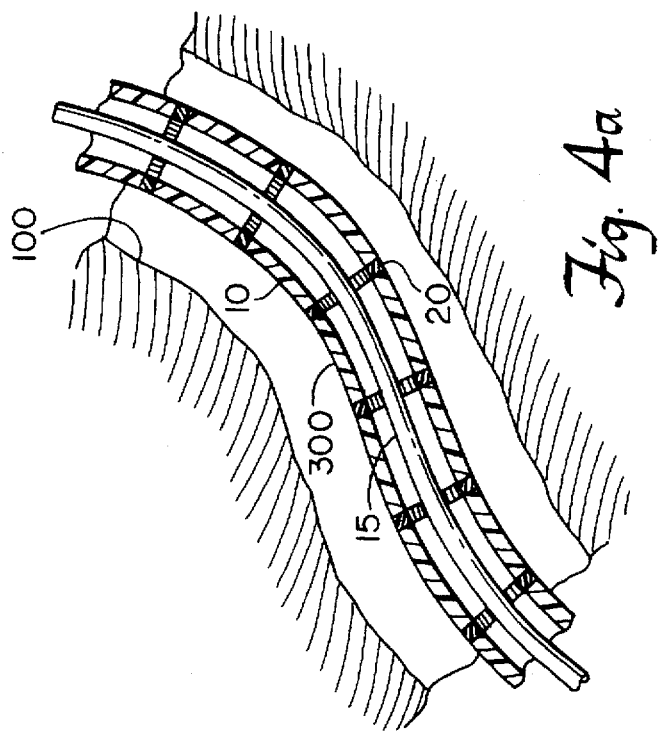
FIG. 4a illustrates the interior of the tube of the invention.
Figure 4:
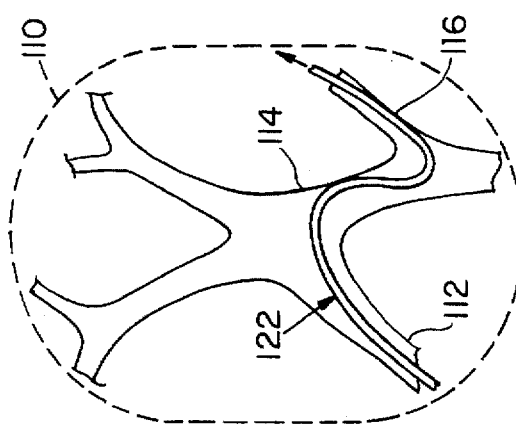
FIG. 4 illustrates the placement of the flexible, non-collapsible tube of the invention in a body lumen.

FIG. 4 illustrates the placement of the flexible, noncollapsible tube of the invention. Section 110 illustrates target tissue which includes a portion of a small vessel, tortuous pathway which must be traversed to reach a selected target site. Vessel 112 branches into vessel 114 and vessel 116 branches from vessel 114. Tube 122 represents a flexible, noncollapsible catheter structure in accordance with the invention. As can be seen from FIG. 4, the catheter easily conforms to the tortuous, small blood vessel path. Moreover, the hardened sections of catheter 122 prevents collapse regardless of the pressures residing at the interior or exterior of the tube.

The tube can be extruded in soft polyurethane and then submitted locally to an intense ultraviolet light which would locally harden sections of the tube to a higher durometer, such as 80 or 90 Shore A. The tube would retain its original softness everywhere except in those areas that have been treated. Thus, the unhardened part of the tube will add the flexibility needed for adequate manipulation of the tube during catheterization procedures or to navigate around tight vascular corners. The hardened rings or helical sections will prevent the collapse of the tube under outside pressure. The tube's resistance to collapse permits long term in vivo use. Localized heating could also create this perfectly smooth plastic catheter which is flexible and noncollapsible. The hardened catheter can be removed from the patient by pulling on the device.

FIG. 4a illustrates the interior of the catheter 300 when in use in a body lumen 100. Fiber optic 15 can be used to transmit light to diagnose disease, to ablate tissue, to harden the tube sections, and to sterilize the catheter. Catheter 300 is comprised of hardened sections 20 and flexible sections 10.

Figure 5:
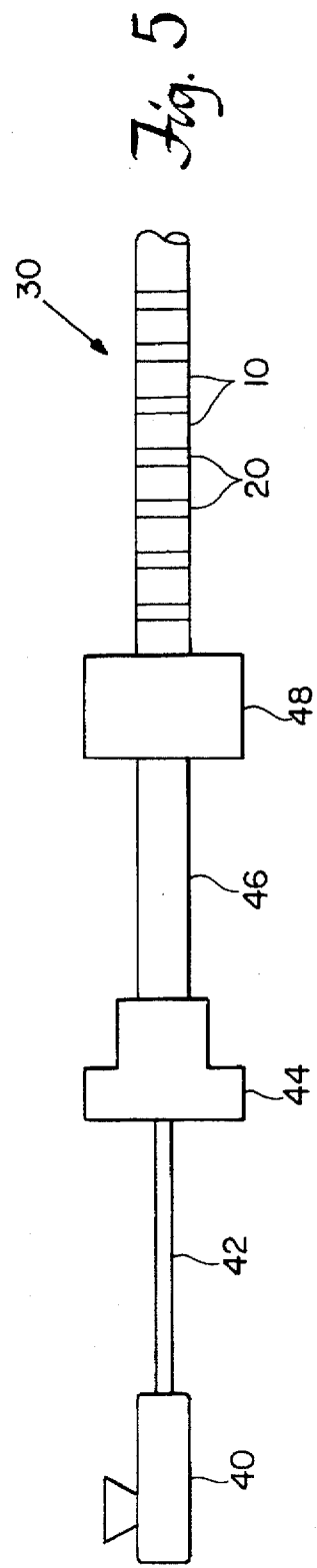
FIG. 5 illustrates an extrusion device for manufacturing the flexible, non-collapsible tube of the invention comprised of a hardened area of the same composition as the flexible area.

FIGS. 5 and 6 illustrate inexpensive simple techniques for manufacturing flexible tubing with noncollapsible hardened sections. For example, FIG. 5 shows an apparatus for creating a single composition tube. Extruder 40 directs the plastic polymer material of the tube 30 along pipe 42 to a tubing die 44. Unformed tube 46 is extruded from tubing die 44 and is conveyed to a radiation source 48. Radiation source 48 exposes portions of unformed tube 46 to create hardened sections 20 interspersed with flexible sections 10. A source of thermal energy would be substituted for the radiation source 48. FIG. 5 shows the creation of ring shaped hardened regions. Radiation source 48 can also expose a helically shaped area to harden a portion of tube 30 into a helix.

FIG. 6 illustrates an apparatus for making a flexible, noncollapsible catheter comprised of a first flexible material and a second harder material. Extruder 40 forces a soft material through pipe 42 to the casting/injection molder 54. Extruder 50 forces a harder second material through pipe 52 to the casting/injection molder 54. The harder higher durometer material is interspersed with the low durometer polyurethane from extruder 40. Tube 30 which is conveyed out of molder 54, is a composite of the softer polyurethane areas 10 and the harder higher durometer material areas 20. Radiation source 55 exposes the higher durometer material in regions 20 and further hardens those segments of the catheter. As in the FIG. 5 embodiment, a source of thermal energy can be substituted for the radiation source 55. Also, a rotary die extruder can be substituted for casting/injector molder 54 to produce a spiral or helical hardened area. By using a rotary die extruder, the main body of the tube is made of a soft material, extruded continuously, with a reinforcing spiral of a harder material pump in the main body of the tube to reinforce it.

Figure 7D:
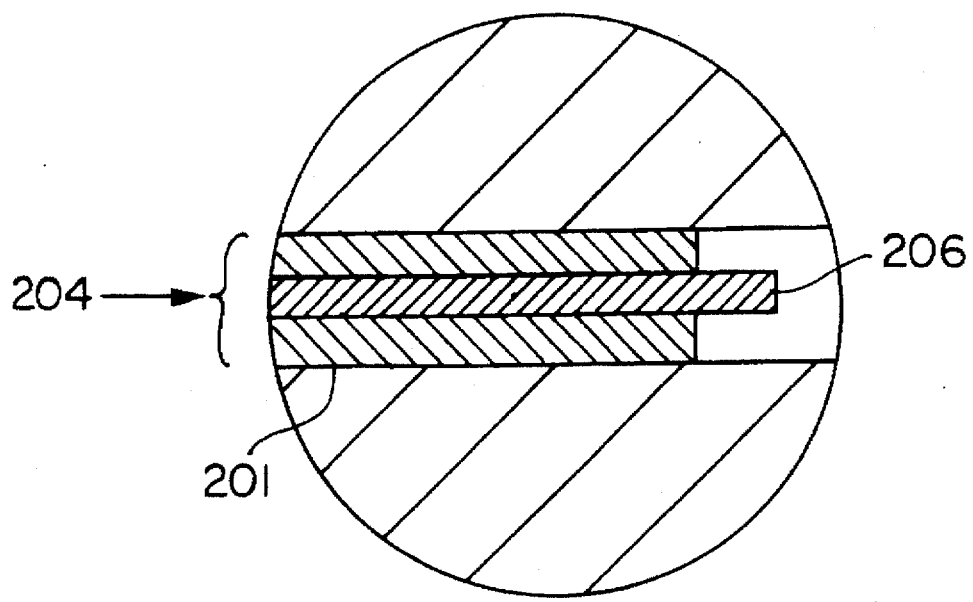
FIG. 7(d) is an enlarged view of the cross section of FIG. 7(a) illustrating an optical fiber which is clad along its length and having a tip which is unclad.
Figure 7E:
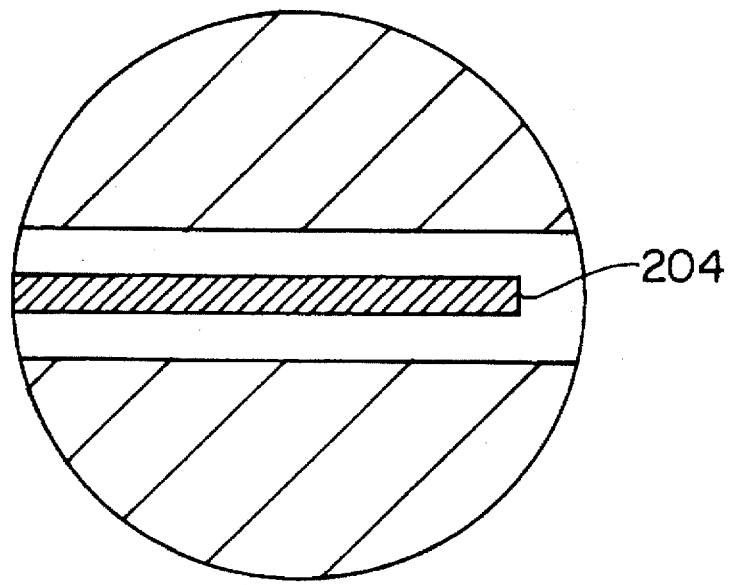
FIG. 7(e) is an enlarged view of the cross section of FIG. 7(a) illustrating a fiber optic which is unclad throughout its length.

FIGS. 7(a) and 7(b) illustrate a catheter which can be sterilized in vivo. The transparent catheter 200 contains fiber optics 202 and 204 along the length of its wall. The fiber optics can be fixed in the wall of the catheter or movable along the length of the catheter. The body of catheter 200 may, or may not be hardened in accordance with the previous discussions. The fiber optics 202 may be provided without cladding so as to let light escape axially. The fiber optics are connected to a source of ultraviolet light 206. To sterilize in vivo, a solution which conducts ultraviolet light such as a saline solution is sent along the catheter interior and the ultraviolet light is activated. The ultraviolet light sterilizes the catheter interior and the body tissue surrounding the catheter, especially tissue at the point of entry into the body. As a result, the risk of infection is reduced. This five minute process need only be performed once every twenty-four hours to be effective. Alternatively the fiber optics can be provided with cladding 201 along its length (as in fiber optic 202) or it can be segmented (as shown in the enlarged view of FIG. 7(c), wherein a portion 205 of the cladding 201 of fiber optic 204 is removed around core 203). In the embodiment illustrated in the enlarged view of FIG. 7(d), the optical fiber 204 is provided with cladding 201 along its length and the tip 206 of the fiber 204 is unclad. The embodiment illustrated in the enlarged view of FIG. 7(e) includes a fiber optic 204 which is unclad throughout its length. Thus, by moving the unclad portions of the fiber along the length of the catheter, selected areas can be sterilized or hardened.

FIG. 7(b) illustrates a horizontal cross sectional view of the catheter with combined fiber optics. One or two fiber optics can be used for sterilization.

Equivalents

Those skilled in the art will recognize, or be able to ascertain, using no more than routine experimentation, many equivalents to the specific embodiment described herein.

The invention is also applicable to tracheostomy or endotracheal tubing. These tubes can also be hardened in situ or in vivo after insertion with ultraviolet light, beamed in a controlled segmental fashion to produce precisely hardened segments to produce a molded tubing, adapted to a given patient's anatomy. For example, dedicated optical fibers as in FIG. 7(a), with the cladding and which are moveable along the length of the catheter can be used to harden the tube at selected locations, as well as to sterilize tissue at selected locations.

These and all other equivalents are intended to be encompassed by the following claims.

I claim:

1. A flexible, indwelling catheter and optical fiber assembly for positioning adjacent body tissue comprising:

a catheter comprising a hollow elongated body with a wall; and an optical fiber comprising a body and a face, the fiber body provided with cladding along its length, the optical fiber extending axially along and within the body wall of the catheter, a segment of the fiber body being unclad to transmit sterilizing light radially throughout the catheter body for sterilization of the catheter and radially-surrounding body tissue.

2. The catheter of claim 1, further comprising a solution disposed within the hollow elongated catheter body for conducting said light throughout the catheter.

3. The catheter of claim 2 in which the solution is a saline solution.

4. A catheter, as recited in claim 1, wherein the fiber is slidably mounted in the catheter body wall such that it is movable along the length of the catheter.

5. A catheter, as recited in claim 4, wherein the fiber includes a tip and wherein a majority of the length of the fiber body is clad with light opaque material and wherein the fiber body at the tip and said segment is unclad.

6. A catheter, as recited in claim 1, wherein the fiber body comprises a plurality of clad segments separated by unclad segments.

7. A catheter, as recited in claim 1, wherein a majority of the fiber body is unclad.

8. A catheter, as recited in claim 1 in which the catheter further comprises an additional radio-opaque material.

9. A flexible, indwelling catheter and optical fiber assembly comprising:

a catheter comprising a hollow elongated body with a wall; and an optical fiber comprising a body and a face, said fiber slidably mounted in the catheter body wall and movable along the length of the catheter, the fiber body provided with cladding along its length; a segment of the fiber body being unclad to transmit ultraviolet light radially through the catheter body for in vivo sterilization of the catheter and radially-surrounding body tissue.

10. A catheter, as recited claim 9, wherein the optical fiber includes a tip and wherein a majority of the length of the fiber body is clad and wherein the fiber body at the tip and said segment is unclad.

11. A catheter, as recited in claim 9, wherein the fiber body includes a plurality of clad segments separated by unclad segments.

12. A catheter, as recited in claim 9, wherein a majority of the fiber body is unclad.

13. A flexible, indwelling catheter and optical fiber assembly for in vivo positioning comprising:

an ultraviolet light source;

a catheter comprising a hollow elongated body; and an optical fiber slidably mounted relative to and extending along the body of the catheter, the fiber having a proximal and a distal end, the proximal end of the fiber being coupled to the ultraviolet light source, the fiber comprising a body and a face, the fiber body provided with cladding along its length, a segment of the fiber body being unclad to transmit ultraviolet light transmitted from the ultraviolet light source through the fiber body and radially outwardly from the fiber body against the adjacent catheter for sterilization of the catheter.

14. A catheter, as recited in claim 13, wherein the optical fiber includes a tip at the distal end and wherein a majority of the length of the fiber body is clad and wherein the optical fiber body at the tip and said segment is unclad.

15. A catheter, as recited in claim 13, wherein the fiber body includes a plurality of clad segments separated by unclad segments.

16. A catheter, as recited in claim 13, wherein a majority of the fiber body is unclad.

17. A flexible indwelling catheter and optical, fiber assembly comprising:

a catheter comprising a hollow elongated body; and an optical fiber comprising a body and a face, the fiber body having a proximal end and a distal end and being clad except at unclad segments intermediate the length of the fiber, the fiber extending along the body of the catheter, such that a portion of ultraviolet light transmitted from the proximal end of the fiber body toward the distal end escapes radially outwardly through the catheter body at the unclad segments for in vivo sterilization of the catheter and radially-surrounding body tissue.

* * * * *